US006947783B2

(12) United States Patent
Immerz

(10) Patent No.: US 6,947,783 B2
(45) Date of Patent: Sep. 20, 2005

(54) SYSTEM FOR THE NAVIGATION-ASSISTED POSITIONING OF ELEMENTS

(75) Inventor: Martin Immerz, München (DE)

(73) Assignee: BrainLAB AG, Kirchheim/Heimstetten (DE)

(*) Notice: Subject to any disclaimer, the term of this patent is extended or adjusted under 35 U.S.C. 154(b) by 489 days.

(21) Appl. No.: 09/808,737

(22) Filed: Mar. 15, 2001

(65) Prior Publication Data
US 2002/0038085 A1 Mar. 28, 2002

(30) Foreign Application Priority Data
Sep. 26, 2000 (EP) .............................. 00120229

(51) Int. Cl.⁷ ............................ A61B 5/05; A61B 19/00
(52) U.S. Cl. ........................................ 600/410; 606/130
(58) Field of Search ................................ 600/410, 426, 600/425, 407, 411; 606/130, 88, 87, 90

(56) References Cited

U.S. PATENT DOCUMENTS 6,235,038 B1 * 5/2001 Hunter et al. ............... 606/130
6,249,713 B1 * 6/2001 Geiger et al. ................ 700/57
6,348,058 B1 * 2/2002 Melkent et al. ............. 606/130
6,381,485 B1 * 4/2002 Hunter et al. ............... 600/407
6,689,142 B1 * 2/2004 Tremaglio et al. .......... 606/130

FOREIGN PATENT DOCUMENTS

WO 97/23172 A 7/1997
WO 99/15097 A 4/1999

OTHER PUBLICATIONS

Kienzle, T.C. et al., "Total Knee Replacement", IEEE Engineering in Medicine and Biology Magazine, US, IEEE Inc., New York, Bd. 14, Nr. 3, 1, May 1, 1995.

* cited by examiner

Primary Examiner—Daniel Robinson
(74) Attorney, Agent, or Firm—Renner, Otto, Boisselle & Sklar, LLP

(57) ABSTRACT

A system for applying an element to a body, wherein the position of a device for preparing and/or producing a connection between said body and said element relative to the position of said body is detected, it also relating to a system for applying an element to a body comprising a device for preparing and/or producing a connection between said element and said body and a position detection device for detecting the position of said device, for preparing and/or producing a connection between said element and said body, and for detecting said position of said body.

9 Claims, 4 Drawing Sheets

SYSTEM FOR THE NAVIGATION-ASSISTED POSITIONING OF ELEMENTS

BACKGROUND OF THE INVENTION

1. Technical Field

The present invention relates to a, more particularly, medical engineering method and system for navigation-assisted positioning of elements, more particularly, for aligning or positioning bone or joint implants, such as for example, in the region of the knee, hip or spinal cord.

The use of jigs is known in implanting artificial knee joints. These are attached to the femur, the thigh bone, and to the tibia, the shin bone, to determine the incision planes of each bone for substantially defining the alignment of the femur and tibia implants. In this arrangement the jigs should as far as possible be positioned such that after siting the implants, the mechanical femur axis and mechanical tibia axis are aligned with one another.

It is the object of the present invention to propose a method and system for applying an element to a body with which the element is positionable as precisely as possible.

This object is achieved by a method and system in accordance with the independent claims. Advantageous embodiments ensue from the sub-claims.

SUMMARY OF THE INVENTION

By the method according to the invention an element, for example a jig or a pilot for an incision device, is precisely applied to a body, such as for example a bone, by navigating a device for preparing and/or producing a connection between the element and the body, for example a drill for producing a hole, or a suitable fastener capable of holding the element to the body, such that the connecting points between the body and the element can be produced with precise positioning. When the element is subsequently applied to the thus prepared or produced connecting points, it is thus automatically in the desired position. Navigating the device for preparing or producing one or more connections or connecting points is preferably achieved by detecting the position of this device relative to the position of the body on which the element is to be applied, or relative to a design position, whereby detecting the position may be achieved both continuously or at given points in time, or intermittently. The difference detected between the actual position and the design position may be either outputted, e.g. visualized on a display, and/or employed directly for auto-navigation.

It is thus not necessary in accordance with the invention to detect the position of an element itself in order to apply this element to a body in a desired position, although of course detecting the position of the element may also be implemented together with the method in accordance with the invention. Aligning or positioning an element on a body is achieved in accordance with the invention by preparing or producing the connection or connecting points precisely positioned between the element and the body, e.g. by navigating a drill, whereby applying the element to the intended connecting points aligns the element precisely positioned.

Preferably, the three-dimensional structure of the body/bodies to which one or more elements are to be applied is mapped. This may be done, for example, by computer tomography, magnetic resonance imaging or other known methods, it thereby being possible to scan the complete body, although only the portions of the body of interest or relevance need be scanned. In this arrangement, portions or structures of the body not scanned can be established, for example, by interpolation. Thus, for example, a small portion of the hip, of for example 5 cm, of the knee, of for example 10 cm, and of the bone or upper ankle joint, of for example 5 cm, may be scanned in sequence by computer tomography, to obtain the data relevant for precisely positioning an element from these scans. The spacing between the individual scans can be obtained, for example, from the movement of a table resting the leg of the patient, thus mapping from these three portion scans the anatomical axes of the leg, i.e. the actual orientation of bones and joints, as well as the mechanical axes, i.e. the orientation of supporting lines. In general, only the portion of the body of interest for applying an element need be mapped, if it can be established from suitable additional information, such as for example the location of the individual scans relative to each other, how the structures relevant to applying the element are oriented.

Advantageously, a data model of the body/bodies to which one or more elements are to be applied is generated, to permit implementing by way of this data model with, for example, suitable software, methods for enhancing the scan quality, or other imaging methods, methods for virtualization of relevant portions, or the like.

Preferably, a plurality of in particular three-dimensional data models of an implant, for example data models of various implants, is made available. This may be, for example, a library of implants or prostheses of various dimensions, whereby one or more data models of one or more implants may be selected.

Advantageously, in particular by using the scan data or the generated data model of the body, an implant such as for example a prosthesis, is positioned in a virtual relationship to the body, i.e. a knee implant for example is virtually implanted. Positioning may be implemented both automatically, i.e. for example by means of a programmed algorithm—the implant preferably being positioned so that when sited the main load points correspond with the mapped mechanical axes of the body/bodies, for example the mechanical femur axis and the mechanical tibia axis—and manually, i.e. for example by outputting or displaying data so that by making suitable entries the implant or prosthesis can be positioned or repositioned manually. Preferably, a combined method is implemented in which firstly a position is proposed by a suitable algorithm or software, with the possibility of the proposed position being subsequently changed manually. In this arrangement, siting the implant can be fine-tuned by shifting, turning, or increasing or reducing it in size.

Advantageously, the desired or design position of the element to be applied is established from the position of the implant, i.e. the position of the element to be applied to or implanted to the body can be determined from the fixed locational relationship between the body and the implant to be implanted into or attached onto the body. When, for example, an artificial knee joint is to be implanted, the desired position of the knee joint to be implanted likewise defines the position of, for example, a jig used for this purpose to determine the incision plane on a bone, whereby this incision plane may serve as a locating face for the artificial knee joint. More particularly, it is of advantage to know the position of certain elements or portions of the jig or the element to be applied, such as for example the position of holes in the jig for controlling or monitoring through these data the positionally precise drilling of holes in a bone, which serve to secure the jig.

It is of advantage when aligning, i.e. siting the body clearly defined relative to a fixed system of locations or coordinates and/or the device for producing or preparing the connection between the body and the element to be applied, for example a drill and/or the element, is done automatically. For mapping the body, for example one or more bones of the patient, a variety of methods can be employed. Firstly, for example, markers may be firmly secured to the body to later permit mapping the three-dimensional location of the body by way of the position of these markers. The markers may be, for example, one or more reflecting elements, the position of which is detected by one or more suitable cameras, for example, infrared cameras. It is good practice to use three markers arranged, for example, in the form of an isosceles triangle. Thus, to register the body, for example a bone, with the markers applied thereto relative to the data model of the body scanned, for example by computer tomography or magnetic resonance imaging, a comparison of the surfaces may, for example, be implemented. In this arrangement, a number of points in the data model, for example 20, can be selected at will in an attempt to obtain as precise an agreement between the data model and the real body as possible. It is furthermore possible to perform aligning by one or more scans of the body with the markers applied thereto. Thus, for example, one or more X-ray scans may be produced with a C-bow, by means of which aligning can be performed, there furthermore being the possibility of scanning an arbitrary line on the body with a light source, for example a laser pointer, for performing alignment using the light reflected from the body.

Just as with the body, so the drill or a suitable device for preparing or producing a connection may also be aligned, to which one or more markers may also be provided, whereby for calibration a benchmark, for example, can be pointed to by the tip of the drill, so that the three-dimensional location of the markers relative to the tip of the drill is clearly defined.

Once the position of the body, for example a bone, has been mapped and it has been established at which location, for example, holes are to be drilled in the bone for securing a jig, for example, so that an incision can be made for aligning an implant applied to this incision as desired, then for example a drill whose three-dimensional position is likewise mapped can be navigated so that one or more holes can be drilled at the desired locations. In this arrangement, as mentioned above, it is possible to navigate the drill either automatically or to perform drilling manually, whereby any departure of the drill from, for example, the entry point and/or the drill centerline can be displayed. It is furthermore possible to indicate the drilling depth, an alert signal being given, for example, upon the desired drilling depth being achieved, or the drill automatically being deactivated.

Supplementary thereto, each step in the method can be checked or corrected by fluoroscopic scanning, i.e. by implementing intra-operative scans.

The computer program product in accordance with the invention may be loaded directly into the internal memory of a digital computer and comprises software code sections with which one or more steps of the method as described above can be implemented when the product is run on a computer.

Furthermore, the invention comprises a computer program product which is stored on a computer-compatible medium and comprises a computer program product as a computer-readable program as outlined above.

The system in accordance with the invention, for applying an element to a body, comprising a device for preparing and/or producing a connection between the element and the body and a position detection device for detecting the position of the body and of the device. With the system in accordance with the invention, it is thus possible to locate the device for preparing or producing the connection relative to the body, to thus permit automatic navigation of the device, or a signal output indicating a possible deviation from position.

A drill, a saw or some other device for working or changing the surface of the body, or also a device for applying special fasteners, such as for example pins, clips, adapters or suitable connector elements may, for example, be used as the device for preparing a connection. The device for producing a connection may be, for example, a device for applying a nail, a screw, a pin, a clip or some other suitable fastener, directly producing a connection between the body and the element, it also being possible to prepare or produce other types of connection, such as for example a bonded connection.

The position detection device may be realized by one or more optical mapping elements, such as for example infrared cameras or other suitable means for mapping, e.g. ultrasound, radio or other suitable signals for visualizing the three-dimensional position of an object.

Preferably, one or more markers are applied to the body and/or to the device for preparing or producing the connection, wherein these markers can be mapped by the position detection device, thus making three-dimensional mapping possible with no contact. It is, however, just as possible to detect the position three-dimensionally by some other means, for example by connecting the object to be mapped to a benchmark by means of a connecting element, which by analyzing its curvature or bend provides an indication as to the location of its end point relative to its starting point. For example, a multi-jointed arm with location sensors on each of the joints or a glass-fiber cable may be used, providing an indication of its three-dimensional profile from the diffraction and refraction of light passed through it.

It is advantageous to provide a processor capable of, for example, receiving and analyzing the signals detected by the position detection device, in order to align the object with the markers applied to it relative to a data model of the body obtained prior, for example by computer tomography or magnetic resonance imaging. In addition, the processor may serve to prepare or implement one or more of the steps in the method described above.

Preference is given to providing an optical display, for example a screen connected to the processor, for outputting data or images corresponding to the respective operating condition of the system, such that for example a three-dimensional model of the body can be displayed with an element positioned virtually therein, or with which potential deviations in the position of the device for preparing or producing the connection between body and element can be displayed.

It is further advantageous to provide an input device, such as for example a keyboard whereby the input device may also be combined with the display device, for example in the form of a touch-screen. Via this input device, the virtual positioning of the element on the body can, for example, be varied, or implementation of one or more of the steps in the method as described above be activated and/or corrected or terminated.

Preferably, a data recording device for recording data during operation of the system is provided, for example for later documentation of an implemented method.

BRIEF DESCRIPTION OF THE DRAWINGS

The invention will now be detailed by way of a preferred embodiment with reference to the Figures, in which.

DESCRIPTION OF THE PREFERRED EMBODIMENTS

Figure 1:
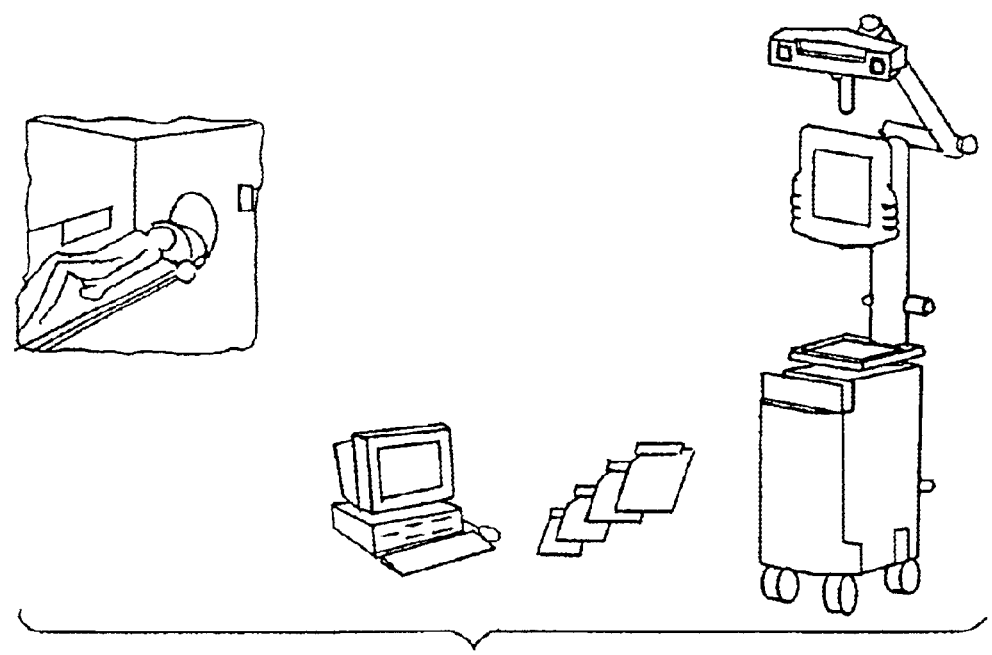
FIG. 1 illustrates how the data of a body are detected, in order to generate a data model.
Figure 2:
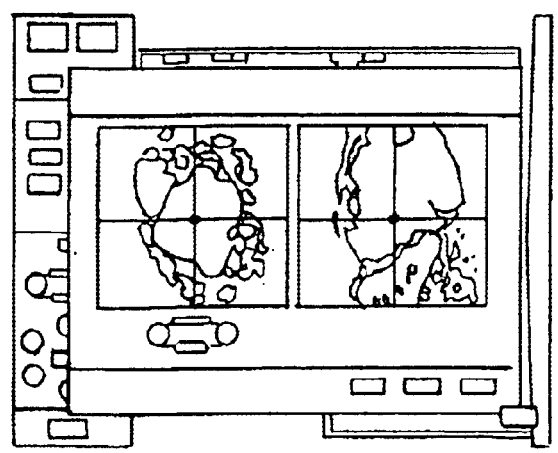
FIG. 2 illustrates how the mechanical axes of the mapped body in the data model are obtained, such as are relevant to positioning an implant.

FIG. 1 illustrates how the data are detected by, for example, scanning the hip, knee and ankle bone or joint of a patient in a computer tomograph. In this arrangement, the position of the table resting a patient, for example, is detected in each scan, to permit locating the individual scans relative to each other. The recorded data are transmitted, for example via a data network or suitable data carrier, to an analyzer with which the data can be further processed as shown schematically in FIG. 2.

By suitable software for example, the mechanical axis of the mapped bodies is obtained, for example the mechanical femur axis as definable by the thigh head and the mass center-point of the joint head, i.e. the parts of the femur in contact with the tibia or shin bone during movement of the joint. Likewise detected is the mechanical tibia axis as determined by the mass center point of the proximal tibia, i.e. of the proximal part of the bone, and the mass center point of the talus or ankle bone. As evident from FIG. 2, the detected mass center-points can be displayed on a screen for any incision displayed.

Figure 3:
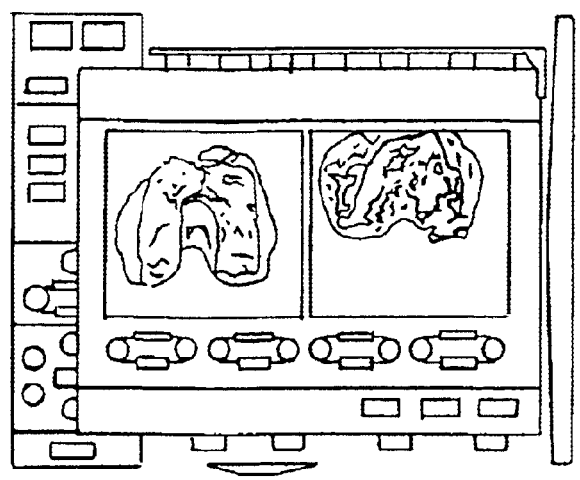
FIG. 3 illustrates virtual positioning of the implant in the data model.

FIG. 3 illustrates how the position of a femur implant is established virtually, as selected from a stored data base or library of multiple implants. The position of the implant as proposed by an algorithm permits further manual change, i.e. shifting or turning in the virtual model.

Figure 4:
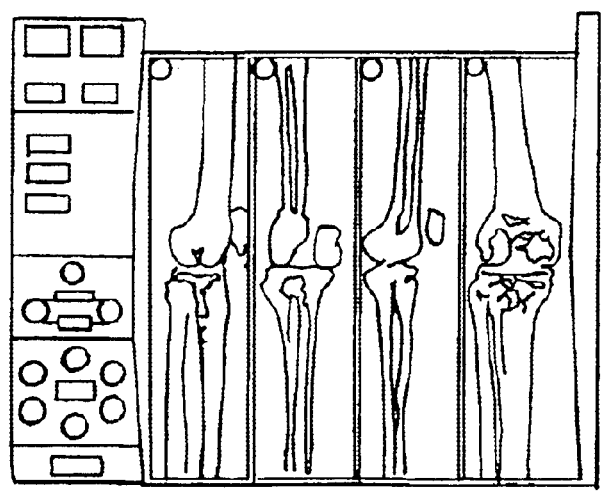
FIG. 4 illustrates the display of the mechanical axes according to the virtual positioning of the implant.

FIG. 4 illustrates how the correct position of the implant is checked, the display showing the mechanical axis with the integrated implant, in order to implement a preoperative check of the correct position. On completion of checking or, where necessary, after repositioning and verifying the correct location of the implant, the method in accordance with the invention can be implemented.

Figure 5:
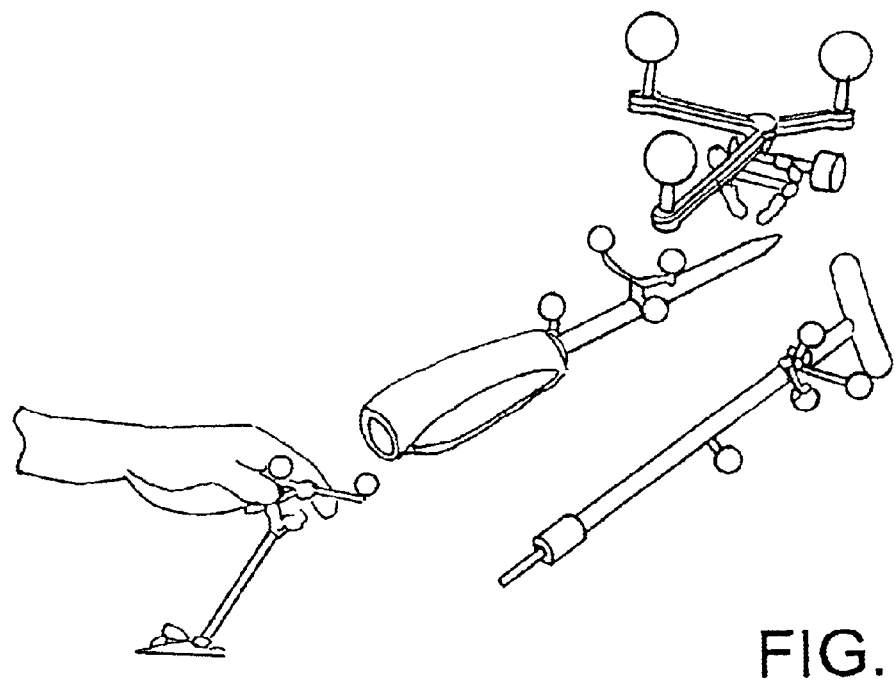
FIG. 5 shows an adapter clip with a three-marker fiducial spider arranged thereon.

FIG. 5 illustrates how, in addition, adapter clips can be secured to any instrument as required, to detect the three-dimensional location of the instrument or for implementing a suitable navigation.

Figure 6:
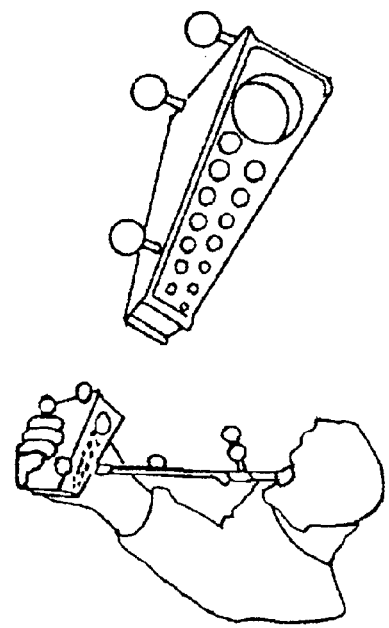
FIG. 6 shows an instrument calibration matrix.

FIG. 6 illustrates how an instrument having markers attached thereto can be calibrated by means of a calibration matrix likewise provided with markers and comprising defined holes of differing sizes. By inserting the tip of an instrument into a defined hole of the calibration matrix, the position of the instrument tip relative to the markers fixed to the instrument can be detected.

Figure 7:
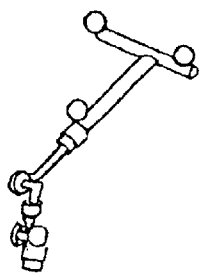
FIG. 7 shows a three-marker fiducial spider element as applicable to a body.

FIG. 7 illustrates how fiducial elements may be secured to the body, for example to the distal femur, i.e. the part of the bone more remote relative to the torso, and the proximal tibia, by means of screws. These secured fiducial elements serve to precisely map the three-dimensional location of the body, for example of one or more bones.

Figure 8:
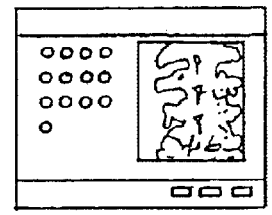
FIG. 8 is a schematic illustration of one step in implementing aligning.

FIG. 8 illustrates how aligning the body, for example by surface matching, i.e. by comparing specific benchmarks, is achieved. This may also be done by one of the other methods as described above, FIG. 8 merely illustrating schematically as an example how alignment is achieved by surface matching at various benchmarks.

Figure 9:
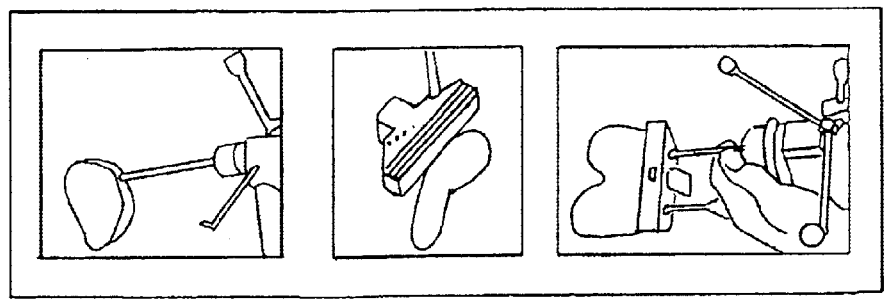
FIG. 9 shows a drill with markers applied thereto in accordance with the invention.
Figure 10:
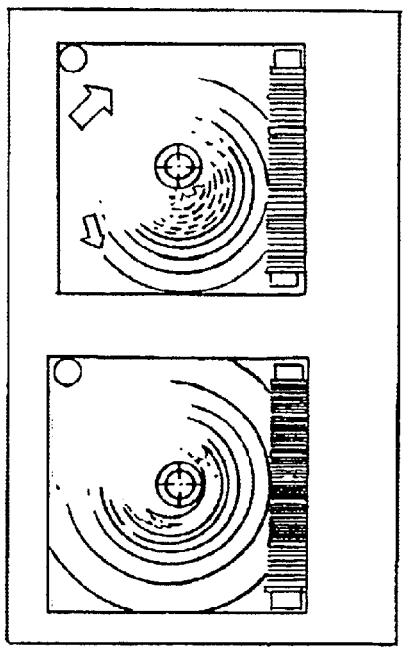
FIG. 10 shows a targeting system for navigating the drill.

Once the body is registered and the implant virtually positioned and, as shown in FIG. 4, checked with respect to being correctly located, the position of a jig, and thus the position of the holes serving to secure the jig, can be detected. A drill with a fiducial element applied thereto, as shown in FIG. 5, and calibrated with a calibration matrix as shown in FIG. 6, can thus be navigated with respect to the registered body, so that the holes serving to secure the jig are drilled such that an incision implemented with the jig into the body or bone reaches the desired position of the implant on the bone. In this arrangement, navigating the drill may be implemented with a targeting system as shown in FIG. 10, the insertion depth being shown on the right-hand side of the targeting system. At the top left, an arrow indicates the angular departure, and at the bottom left, a further arrow indicates the deviation from the position, including a distance indication. By means of the targeting system as shown in FIG. 10 navigating the drill as shown in FIG. 9 may be implemented.

In the foregoing description preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A system for applying an element to a living body, comprising:
   a) a device for physically altering a part of the living body to prepare and/or produce a connection between said element and said living body; and
   b) a position detection device (i) for detecting a position of said device for physically altering a part of the living body to prepare and/or produce a connection between said element and said living body, and (ii) for detecting a position of said living body, wherein plural markers are applied to said device for physically altering for three-dimensional tracking of said device for physically altering.

2. The system as set forth in claim 1, wherein said device for preparing and/or producing a connection between said body and said element is a drill, a saw, a surface-working device, a screwing device or a nailing device.

3. The system as set forth in claim 1, wherein said position detection device detects optical, acoustical and/or radio signals.

4. The system as set forth in claim 1, wherein one or more markers are applied to said body.

5. The system as set forth in claim 1, wherein a processor is provided for preparing or implementing one or more of the steps in a method comprising: detecting the position of a device for preparing and/or producing a connection between said body and said element relative to the position of said body.

6. The system as set forth in claim 1, wherein a display device is provided, connected to said processor.

7. The system as set forth in claim 1, wherein an input device is provided, connected to said processor.

8. The system as set forth in claim 1, wherein a data recording device is provided for recording data during the operation of said system.

9. The system as set forth in claim 1, comprising means for applying the element to the prepared or produced connection, wherein the means for applying the element to the prepared or produced connection aligns the element to the body.

* * * * *